US00PP26599P2

(12) United States Plant Patent
Moore

(10) Patent No.: US PP26,599 P2
(45) Date of Patent: Apr. 12, 2016

(54) ***SARCOCOCCA* PLANT NAMED 'PMOORE03'**

(50) Latin Name: *Sarcococca hookeriana*
Varietal Denomination: PMOORE03

(71) Applicant: Peter Robert Moore, Hampshire (GB)

(72) Inventor: Peter Robert Moore, Hampshire (GB)

( * ) Notice: Subject to any disclaimer, the term of this patent is extended or adjusted under 35 U.S.C. 154(b) by 222 days.

(21) Appl. No.: 13/998,667

(22) Filed: Nov. 21, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

Garden & Hardware News—Retail Plants & Shrubs retrieved on Aug. 20, 2015, retrieved from the Internet at <http://content.yudu.com/Library/A1svig/GardenampHardwareNew/resources/32.htm> pp. 32-33 (2011).*
Crocus. *Sarcococca hookeriana* Winter Gem 'Pmoore03', retrieved on Aug. 24, 2015, retrieved from the Internet at <http://www.crocus.co.uk/plants/_/sarcococca-hookeriana-winter-gem-pmoore03-pbr/classid.2000020895/> 1 page.*

* cited by examiner

*Primary Examiner* — June Hwu
(74) *Attorney, Agent, or Firm* — Penny J. Aguirre

(57) ABSTRACT

A new cultivar of *Sarcococca* named 'PMOORE03', that is characterized by its broad glossy foliage that is persistently dark green in color, its free flowering habit with fragrant flowers that have white stamens and reddish pink tepals, its ability to grow well in containers, and its moderate growth rate with good growth observed when grown in a range of light conditions from light shade to full sun.

2 Drawing Sheets

Botanical classification: *Sarcococca hookeriana*.
Variety denomination: 'PMOORE03'.

BACKGROUND OF THE INVENTION

The present invention relates to a new and distinct cultivar of *Sarcococca hookeriana*. The new cultivar will be referred to hereafter by its cultivar name, 'PMOORE03'. 'PMOORE03' is an evergreen shrub grown for use as a landscape plant and ornamental garden plant.

The new cultivar was derived from a controlled breeding program by the Inventor in Longstock, England. The objective of the breeder was to develop a new cultivar of *Sarcococca* that performs well in a container. The Inventor made a cross in summer of 2004 between *Sarcococca hookeriana* var. *digyny* 'Purple Stems' (not patented) as the female parent and an unammed proprieary plant of *Sarcococca hookeriana* var. *humilis* from the Inventor's breeding program as the male parent. The Inventor selected 'PMOORE03' in 2007 as a single unique plant amongst the seedlings that resulted from the above cross.

Asexual propagation of the new cultivar was first accomplished by semi-ripe stem cuttings in Longstock, England in 2007 by the Inventor. Asexual propagation by semi-ripe stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PMOORE03' as a unique cultivar of *Sarcococca*.

1. 'PMOORE03' exhibits broad glossy foliage that is persistently dark green in color.
2. 'PMOORE03' exhibits a free flowering habit with fragrant flowers that have white stamens and reddish-pink tepals.
3. 'PMOORE03' performs well when container grown (typical plants of *Sarcococca hookeriana* do not thrive when container grown).
4. 'PMOORE03' exhibits a moderate growth rate with good growth in a range of light conditions from light shade to full sun (plants of *Sarcococca hookeriana* typically do not tolerate full sun).

The female parent of 'PMOORE03', 'Purple Stems', differs from 'PMOORE03' in having leaves that are narrower and a paler shade of green in color, in being more difficult to propograte, and in taking longer to produce a quality plant. The male parent of 'PMOORE03', a unnamed plant of *Sarcococca hookeriana* var. *humilis*, differs from 'PMOORE03' in having a more compact plant habit and in having a slower growth habit. 'PMOORE03' can be most closely compared to the Sarcococca cultivars 'Sarsid 2' (U.S. Plant Pat. No. 19,951) and 'Sarsid 1' (U.S. Plant Pat. No. 19,942). 'Sarsid 2' differs from 'PMOORE03' in having oblanceolate leaves, more vigourous growth habit and a more compact plant habit. 'Sarsid 1' differs from 'PMOORE03' in having leaves that are narrow, oblanceolate to elliptic in shape, in having a more vigourous growth habit, and a groundcover plant habit.

BRIEF DESCRIPTION OF THE DRAWINGS

The accompanying colored photographs illustrate the overall appearance and distinct characteristics of the new *Sarco-*

*cocca*. The photographs were taken of a three year-old plant of 'PMOORE03' as grown in an unheated greenhouse in Boskoop, the Netherlands.

Figure 1:
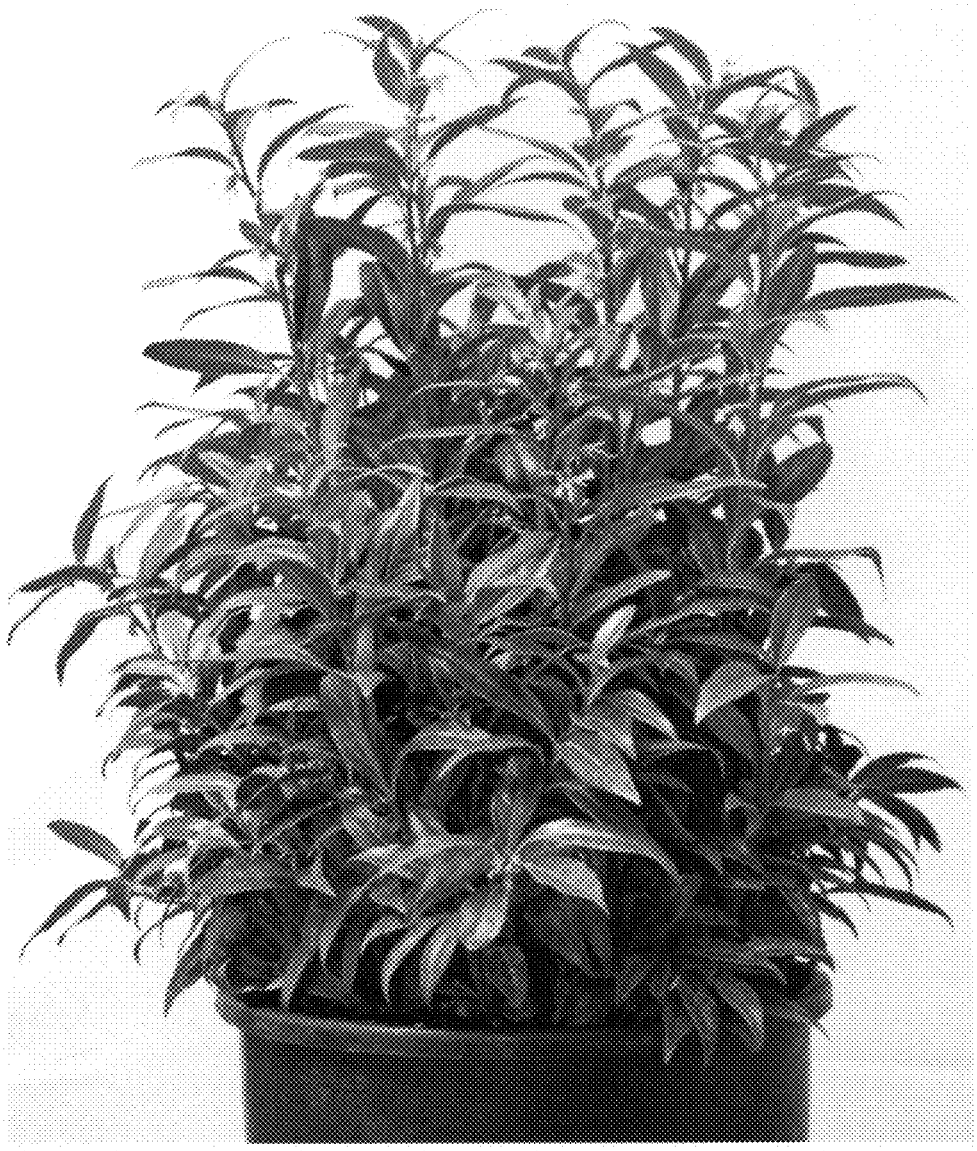

The photograph in FIG. 1 provides a side view of a plant of 'PMOORE03'.

Figure 2:
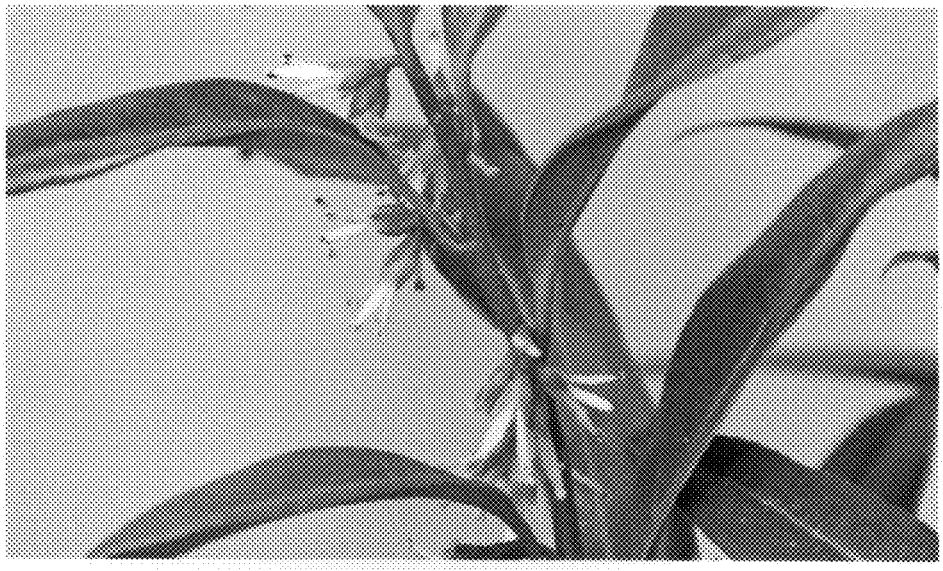

The photograph in FIG. 2 provides a close-up view of the inflorescences of 'PMOORE03'.

Figure 3:
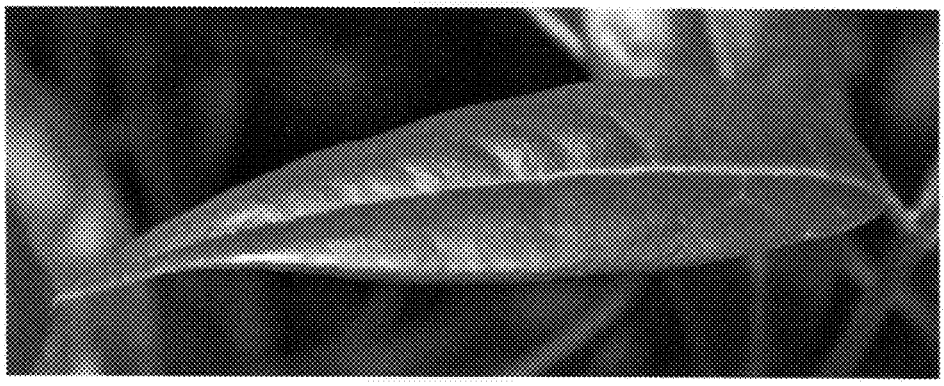

The photograph in FIG. 3 provides a close-up view of the foliage of 'PMOORE03'.

The colors in the photograph may differ slightly from the color values cited in the detailed botanical description, which accurately describe the colors of the new *Sarcococca*.

DETAILED BOTANICAL DESCRIPTION

The following is a detailed description of three year-old plants of the new cultivar as grown in an unheated greenhouse in 30-cm containers in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—January to March in Lockstock, England.

*Plant habit*.—Perennial, evergreen shrub with a broad spreading-upright habit.

*Height and spread*.—An average of 70 cm in height and 60 cm in spread in 5 years in the garden.

*Cold hardiness*.—U.S.D.A. Zone 7.

*Diseases and pests*.—Not more susceptible to pests and diseases than other *Sarcococca* varieties.

*Root description*.—No root structures.

*Propagation*.—Semi-ripe cuttings.

*Time required for root development*.—Approximatley 1 year to finish in a 1.5-liter container or larger from cuttings.

*Growth rate*.—Moderate, performs well in containers.

Stem description:

*Shape*.—Rounded.

*Stem size*.—Lateral branches; about 24.4 cm in length and 0.3 cm in width.

*Stem color*.—A blend of 183A to 200B, closest to 183A.

*Stem aspect*.—Lateral stems an average angle of 80° to horizontal.

*Stem strength*.—Very strong.

*Stem surface*.—Glabrous.

*Internode length*.—Average of 1.9 cm.

*Branching*.—Strong basal branching and moderate lateral branching, and an average of 76 lateral branches.

Foliage description:

*Leaf shape*.—Lanceolate.

*Leaf division*.—Simple.

*Leaf base*.—Short attenuate.

*Leaf apex*.—Long acute.

*Leaf fragrance*.—None.

*Leaf venation*.—Anastomosing, color upper surface; main vein 148D and other veins a blend of N137A and 147B (slightly darker) color lower surface; 144C.

*Leaf margins*.—Entire.

*Leaf arrangement*.—Alternate.

*Leaf attachment*.—Petiolate.

*Leaf surface*.—Upper surface; smooth and glossy, lower surface; smooth and very slightly glossy.

*Leaf size*.—Average of 8.3 cm in length and 2.1 cm in width.

*Leaf quantity*.—Average of 13 leaves per stem 24.4 cm in length.

*Leaf color*.—Newly expanded leaves; upper surface a blend of 144A and 146A, lower surface 146C and 146D, mature leaves; upper surface a blend of N137A and 147A (but darker), lower surface a blend of 137B and 147B.

*Petioles*.—About 1.0 mm in length and 1.2 cm in width, a blend of 144C and 176B in color, surface glabrous.

*Stipules*.—None.

Inflorescence description:

*Inflorescence type*.—Clusters consiting of male and female flowers from axillary nodes, with female flowers positioned basally under the male flowers in the clusters.

*Flower fragrance*.—Strongly fragrant, sweet and pleasant.

*Lastingness of inflorescence*.—Average of 2 weeks, self-cleaning.

*Flower quantity*.—Average of 3 male flowers and 2 female flowers per inflorescence and an average of 50 flowers per lateral stem.

*Flower type*.—Single, unisexual, tepalous.

*Flower size*.—Male; average of 7 mm in diameter and 1 mm in depth, female; average of 3 mm in length and 7 mm in width.

*Inflorescence size*.—About 2.7 cm in length and about 1.8 mm in diameter.

*Peduncles*.—About 7 mm in length and 1 mm in diameter, 178B in color, moderately strong, held at an average angle of 50° to vertical and curved downward at an average angle of 120° to vertical, surface glabrous.

*Pedicels*.—None, individual flowers sessile.

*Flower buds*.—Ovate in shape, up to 5 mm in length and 2 mm mm diameter, color; blend of 48B and 180C to 180D.

*Petals*.—None.

*Sepals*.—None.

*Tepals*.—Average of 4, ovate, convexed shape, average length 4 mm and width 2 mm, dull and smooth on both surfaces, rotate arrangement, entire margin, short apiculate apex, color of upper surface when opening; 185D with upper half tinged 150D, lower surface when opening; a blend of 48B and 180C to 180D, color of upper surface when fully opened 185D with tip tinged 150D, lower surface when fully opened a blend of 48B and 180C to 180D, color not fading.

Reproductive organs:

*Gynoecium*.—1 pistil an average of 4 mm in length, 2 stigmas that are cleft shaped and N155C in color, an average of 2 mm in length, ovary 144A in color.

*Androcoecium*.—Average of 4 (ocassionally 5), filaments are NN155C in color and an average of 6 mm in length, anthers are dorsifixed, oblong in shape, an average of 2.5 mm in length and 59B in color, pollen is moderate in quantity and 155C in color.

*Fruit and seed*.—Fruit and seed have not been observed to form to date.

It is claimed:

1. A new and distinct cultivar of *Sarcococca* plant named 'PMOORE03' as herein illustrated and described.

* * * * *